United States Patent [19]

Bollinger et al.

[11] 4,284,575

[45] Aug. 18, 1981

[54] SUBSTITUTED BENZENESULFONYLAZIDES

[75] Inventors: Frederick W. Bollinger; George G. Hazen, both of Westfield, N.J.

[73] Assignee: Merck & Co., Inc., Rahway, N.J.

[21] Appl. No.: 195,997

[22] Filed: Oct. 10, 1980

[51] Int. Cl.³ .......................................... C07C 117/00
[52] U.S. Cl. .............................. 260/349; 260/239 A; 260/141
[58] Field of Search ........................................ 260/349

[56] References Cited

FOREIGN PATENT DOCUMENTS 5148M   6/1967  France ..................................... 260/349
1117128 6/1968  United Kingdom ..................... 260/349

OTHER PUBLICATIONS

FMC Corp. Chem. Abstracts, vol. 65, col. 12064 (1966), (abst. of Netherlands Appl. 6,512,248).
Kondo et al., Chem. Abst. vol. 86, abst. 170882g, (1977).
Chemical Abstracts, Ninth Collective Index, p. 5756CS, (Benzenesulfonylchloride, 4-dodecyl), copyright 1978.

Primary Examiner—John D. Randolph
Attorney, Agent, or Firm—James A. Arno; Hesna J. Pfeiffer

[57] ABSTRACT

Disclosed are substituted benzenesulfonylazides (I) which are useful as diazo transfer reagents.

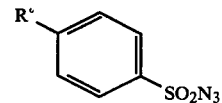

$R° = C_{12}H_{25}$

2 Claims, No Drawings

SUBSTITUTED BENZENESULFONYLAZIDES

BACKGROUND OF THE INVENTION

This invention relates to certain substituted benzenesulfonylazides (I) and processes for their preparation.

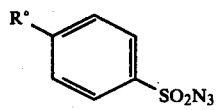

The compounds are useful as a diazo transfer reagent, for examples:

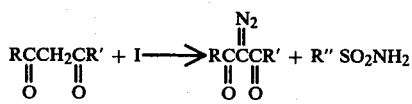

wherein R and R' are, inter alia, alkyl, aryl, cycloalkyl, heterocyclic, aralkyl, lower alkoxy, and alkylthio;

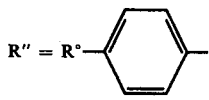

A particularly preferred embodiment of I is p-dodecyl-benzenesulfonylazide (R°=CH$_3$(CH$_2$)$_{11}$—);

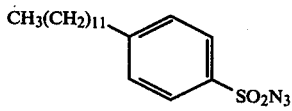

As a diazo transfer reagent, I compares favorably in reaction efficiency with conventionally known diazo transfer reagents but I offers a safety advantage—shock stability and nonexplosiveness. This contrasts with certain azide diazo transfer reagents that are shock sensitive and explosive. In fact, the popular diazo transfer reagent p-tosylazide has the explosive power and shock sensitivity of TNT.

DETAILED DESCRIPTION OF THE INVENTION

The preparation of 1 and a suggestion of its utility as a diazo transfer reagent is given below. With regard to its utility, European Patent Application 79101307.1 (filed 1 May 1979; Publication No. 0007973) is incorporated herein by reference. It is understood that the present diazo transfer reagent 1 can be employed in the diazotization reaction of European Patent Application 79101307.1. The following examples demonstrate this representative utility and describe the preparation of 1. All temperatures are in °C.

EXAMPLE 1

Step A

Preparation of p—C$_{12}$H$_{25}$—benzenesulfonylchloride

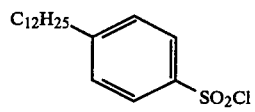

To 50 g (0.153 mole) of technical p—C$_{12}$—H$_{25}$(C$_6$H$_4$)SO$_2$H is added 18.25 g (0.119 mole, 11.1 ml.) of phosphorous oxychloride. The mixture is stirred magnetically while the flask is heated in an oil bath at 75°–80° C. for 1 hr. During this period of heating, the bulk of gaseous HCl evolves at a manageable rate.

Stirring is continued while the flask is heated at reflux with the oil bath maintained at 105°–110° for 16 hrs. The mixture is cooled to room temperature and with the aid of 100 ml of EtOAc, 50 ml of water and 50 g of ice is transferred to a separatory funnel. The EtOAc layer is washed successively with 100 ml portions of ether, 5% NaHCO$_3$ and water. Before discarding, each aqueous extract is shaken in another separatory funnel with 50 ml of EtOAc. Emulsions are broken by adding 5 ml portions of saturated salt solution.

The first water wash required one(1)–5 ml. portion of salt solution; the bicarbonate wash two (2); and the last water wash five (5). With careful separation the water content by KF was reduced to less than 1%. The volume of aqueous extract and discard are measured as a check on the dryness of the final EtOAc solution.

The EtOAc extracts are combined and dried by stirring over 10 g of anhydrous sodium sulfate and 5 g of ammonium sulfate. Lumps of solid should not be allowed to form. The mixture is filtered through a sintered glass funnel precoated with Celite and the cake is washed with EtOAc. If the EtOAc extract is not dry it may filter very slowly at this point. The solution is concentrated in vacuo and pumped. The ratio of the content to the volume of the still should be about 1:10. At higher ratios (for example, 1:5), foaming may be a problem. Alternatively two acetone flushes may be employed. The IR spectrum and tlc behaviour of the concentrate are checked at this point.

On a miniplate (Si Gel G), p—C$_{12}$H$_{25}$—benzenesulfonylchloride, eluted with 1:4 CH$_2$Cl$_2$—hexane, exhibits an Rf of 0.36–40 at room temperature. Material chromatographed over Si Gel G yields the following elemental analysis:

Calcd: C, 62.68; H, 8.47; Cl, 10.28; S, 9.30; O, 9.28.
Found: C, 62.78; H, 8.31; Cl, 10.18; S, 9.34; O, 9.39 diff.

The oily concentrate of the desired p—C$_{12}$H$_{25}$ benzenesulfonylchloride (2) amounts to 49.57 g (93.8% yd). It is a liquid.

No further purification is needed for the next step.

Step B

Preparation of p—C$_{12}$H$_{25}$ benzenesulfonylazide (1)

The sulfonyl chloride (2) 49.57 g., 0.1437 mole) of the previous step is dissolved in 248 ml of acetone and to the solution is added 11.75 g. (0.181 mole) of granular NaN₃. Any lumps of NaN₃ should be broken up. The mixture is stirred at room temperature overnight.

By tlc the reaction is 90% complete in 1 hr. and complete in 2 hrs. On a miniplate (Si Gel G), p—C₁₂H₂₅benzenesulfonylazide (1), eluted with 1:4 CH₂Cl₂—hexanes, exhibits an Rf of 0.18–0.22 at r.t.

The mixture is carefully concentrated in vacuo to avoid foaming and pumped. Alternatively the mixture may be flushed twice with hexanes. The mixture is taken up in hexanes and mixed with 100 g. of silica gel G and filtered thorough 148 g. of additional silica gel G. The first eluate of ca. 200 ml. of hexanes is discarded. This eluant by tlc contains fast running impurities and a small amount of product. The eluate is changed to 1:4 CH₂Cl₂—hexanes and 3,000 ml. collected (u.v. positive). The concentrate of this eluate yields 38.73 g of 1 (72.0% yield) and is essentially a single spot on tlc.

Analysis for: $C_{18}H_{29}N_3O_2S$ (351.52). Calc: C, 61.50; H, 8.32; N, 11.95; S, 9.12; O, 9.10. Found: C, 61.67; H, 8.26; N, 12.17; S, 9.44.

EXAMPLE 2

Preparation of (3S, 4R)-3-[(R)-1-Hydroxyethyl]-4-[3-(4-nitrobenzyl)-oxycarbonyl-2-oxo-3-diazopropyl]azetidin-2-one

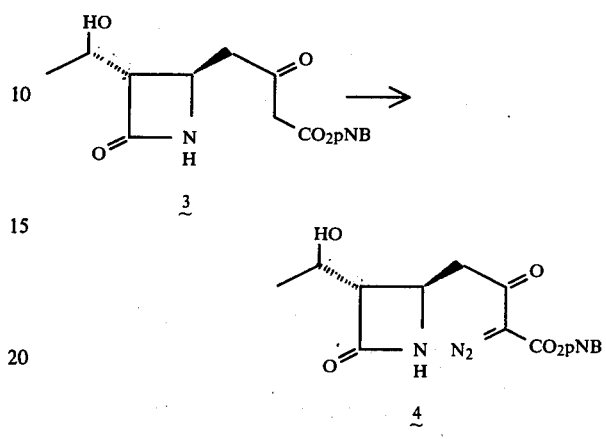

Triethylamine (132 mg, 1.3 mmol) is added by syringe to a mixture of (3S, 4R)-3-[(R)-1-hydroxyethyl]-4-[3-(4-nitrobenzyl)-oxycarbonyl-2-oxopropyl]azetidin-2-one, 3, (253 mg. [0.72 mmol]) and p-dodecylbenzenesulfonylazide (295 mg, 0.84 mmol) in dry acetonitrile (6 ml) at 0° C. When addition is complete the cooling bath is removed and the reaction mixture is stirred at room temperature for 1 hour. The mixture is then diluted with ethyl acetate (50 ml) and filtered. The filtrate is concentrated in vacuo and the residue is chromatographed on a short silica gel column (ethyl acetate) to yield 2.

What is claimed is:
1. A compound having the formula:

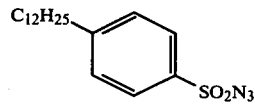

2. p-Dodecylbenzenesulfonylazide:

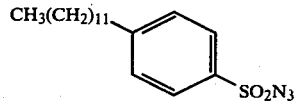

* * * * *